United States Patent

Bjurwill et al.

[11] 3,933,157
[45] Jan. 20, 1976

[54] TEST AND CONTROL DEVICE FOR ELECTROSURGICAL APPARATUS
[75] Inventors: Per Henrik Bjurwill, Bromma; Nils Bertil Jacobson, Solna, both of Sweden
[73] Assignee: Aktiebolaget Stille-Werner, Sweden
[22] Filed: Oct. 23, 1973
[21] Appl. No.: 408,535

[52] U.S. Cl. ......... 128/303.14; 128/423; 317/18 D; 317/31
[51] Int. Cl.² ..................... A61B 17/36; A61N 3/00
[58] Field of Search ..... 128/303.14, 303.17, 303.18, 128/2.1 P, 419 R, 423, 303.13; 317/18 B, 18 A, 18 D, 31

[56] References Cited
UNITED STATES PATENTS

| | | | |
|---|---|---|---|
| 3,303,387 | 2/1967 | Springer | 317/31 |
| 3,628,094 | 12/1971 | Billin | 128/2.1 P |
| 3,683,923 | 8/1972 | Anderson | 128/303.14 |
| 3,723,813 | 3/1973 | Allen | 317/18 B |
| 3,774,106 | 11/1973 | MacPhee | 317/18 B |
| 3,783,340 | 1/1974 | Becker | 317/18 B |

FOREIGN PATENTS OR APPLICATIONS
1,139,927   11/1962   Germany ...................... 128/303.13

*Primary Examiner*—Robert W. Michell
*Assistant Examiner*—Lee S. Cohen
*Attorney, Agent, or Firm*—Hill, Gross, Simpson, Van Santen, Steadman, Chiara & Simpson

[57] ABSTRACT

An electrosurgical apparatus having a diathermy current generator connected to an active electrode and a two-segment inactive electrode in surface engagement with the patient includes a test and control device automatically sensing the sum of the contact impedances of the two inactive electrode segments and inhibiting the passage of the diathermy current through the patient if the sensed impedance value is too high or too low. The sensing of the contact impedances is effected at intervals during periods when no diathermy current flows and is accomplished by means of alternating current.

5 Claims, 2 Drawing Figures

TEST AND CONTROL DEVICE FOR ELECTROSURGICAL APPARATUS

BACKGROUND OF THE INVENTION

1. Field of the Invention

This invention relates to electrosurgical apparatus and more particularly to a test and control device for electrosurgical apparatus.

2. Prior Art

In electrosurgery, also called surgical diathermy, current of high frequency, herein called diathermy current, is used for cutting tissue and coagulating blood to stop bleeding from cut blood vessels. The diathermy current is passed through the patient via two electrodes, an active electrode having a very small contact surface to concentrate the diathermmy current where it passes into the patient and inactive electrode having a large contact surface to reduce the current density where the diathermy current leaves the patient.

If the inactive electrode does not make good contact with the patient's skin, the diathermy current can cause severe burning of the patient at the inactive electrode. The patient may also be burned if the inactive electrode is not at all connected to the patient or to the diathermy current generator and any part of the patient's body makes contact with grounded metal.

The efficient and safe functioning of electrosurgical apparatus thus depends on an unimpaired return of the diathermy current through the inactive electrode. In order that the risk for burns resulting from failure to connect the inactive electrodes to the diathermy current generator, or from any other discontinuity between the inactive electrode and the diathermy current generator, may be reduced some electrosurgical apparatus include a circuit-testing device which upon manual actuation checks the electrical connection between the patient and the inactive electrode. In such apparatus, the inactive electrode is divided into two segments which are electrically insulated from each other and connected in parallel to the diathermy current generator. The circuit-testing device includes a manually actuated switch which when actuated closes a measuring circuit to pass a low-voltage direct current between the two electrode segments via the adjacent portion of the patient's skin. The magnitude of the current is indicative of the conductivity between the patient's skin and the electrode segments and, hence, the ability of the inactive electrode to provide a good return path for the diathermy current.

SUMMARY OF THE INVENTION OF THE DRAWINGS

The improved test and control device according to the invention functions during periods when no diathermy current flows through the inactive electrode back to the diathermy current generator to sense at intervals the sum of the contact impedances of two inactive electrode segments and to inhibit the flow of the diathermy current if the sum of the contact impedances is above or below a predetermined range.

In one form of the invention two silicon controlled rectifiers are connected in series in the energization circuit of a relay which when energized through the normally conducting silicon controlled rectifiers maintains the diathermy current circuit in a condition permitting the diathermy current to pass therethrough. During the testing intervals a 15 kHz current is passed through the two segments of the inactive electrode via the adjacent portion of the patient's skin. If the resulting voltage drop over the electrode segments is above a first predetermined value, one of the two silicone controlled rectifiers is brought to nonconducting condition, resulting in deenergization of the relay and consequent opening of the diathermy current circuit; and if the voltage drop is below a second predetermined value the other silicon controlled rectifier is brought to nonconducting condition with the same result.

DESCRIPTION OF THE PREFERRED EMBODIMENT

Figure 1:
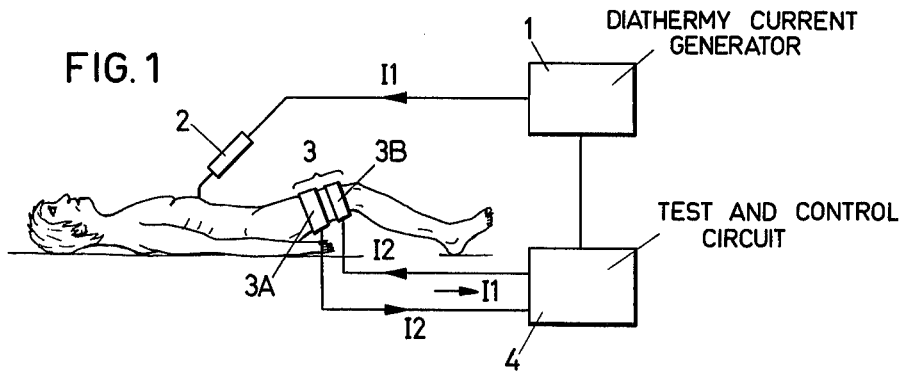
FIG. 1 is a diagrammatic view of an electrosurgical apparatus equipped with a test and control device constructed in accordance with the invention.

Referring to the drawing, FIG. 1 shows an electrosurgical apparatus including a current generator 1 producing a diathermy current I1 the frequency of which is about 1.5 MHz. Typical values of the voltage and amperage are 400 to 500 volts and 1 to 2 amperes, respectively. The diathermy current is fed to an active electrode 2 and passes through the patient and back to the current generator via an inactive electrode 3 comprising a pair of inactive electrode segments 3A and 3B applied to a leg of the patient, and a test and control device 4.

The test and control device 4 funtions to automatically sense the impedance between the two electrode segments 3A and 3B at intervals, namely, during one second at intervals of about ten seconds and to inhibit the passage of the diathermy current I1 between the active electrode 2 and the inactive electrode 3 if the sensed value falls outside a predetermined range. As will appear from the following detailed description the sensing of the impedance is possible only during periods when no diathermy current flows; as long as diathermy current flows, the test and control device 4 is inoperative. The impedance value sensed by the test and control device 4 includes the impedance of the portion of the patient's skin which is engaged by and extends between the electrode segments 3A and 3B. The latter impedance, however, is fairly small in comparison with the total sensed impedance and besides substantially constant, and thus the total sensed impedance is dominated by the sum of the contact impedances of the two electrode segments.

Figure 2:
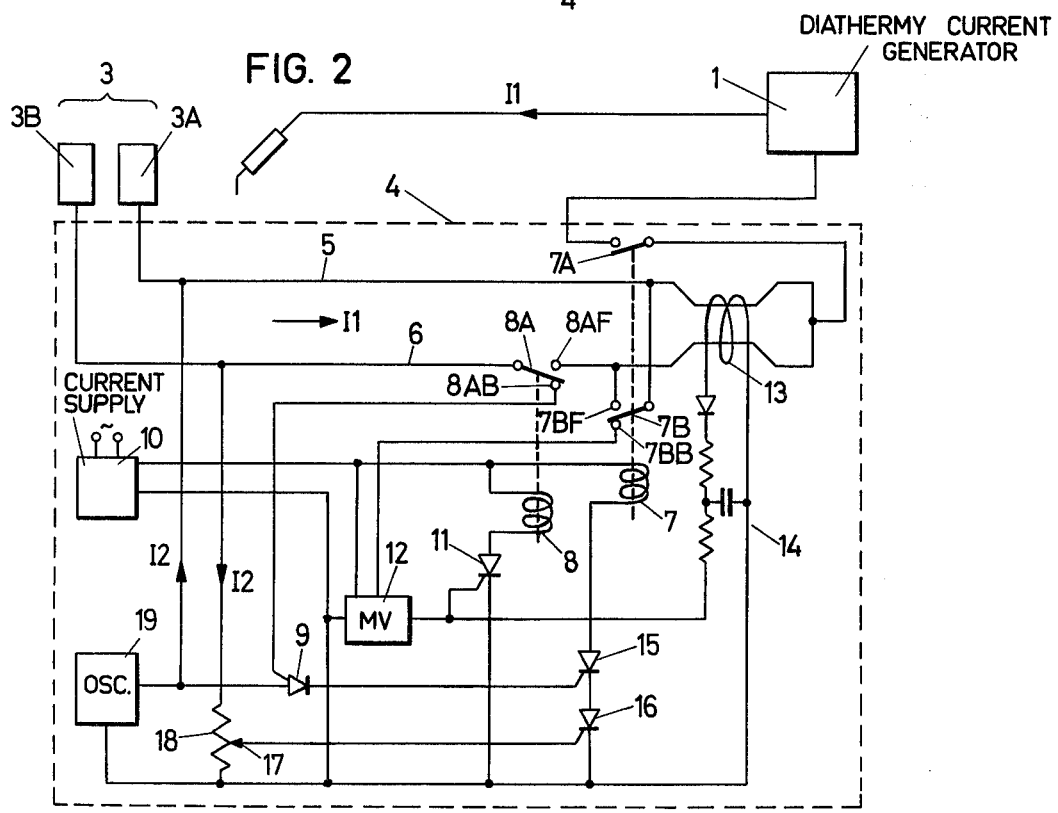
FIG. 2 a similar view including an electrical diagram of the test and control device.

Referring now to FIG. 2, the test and control device 4 includes two leads 5 and 6 connecting the two electrode segments 3A and 3B in parallel to the diathermy current generator 1 through a normally open switch 7A of a relay 7. Inserted in the lead 6 is a switch 8A of a relay 8. In the deenergized condition of the relay 8, the switch 8A closes on a back contact 8AB to connect the electrode segment 3B to the gate of a programmable unijunction transistor 9 and in the energized condition of the relay, it closes on a front contact 8AF to permit diathermy current to pass through the lead 6.

The energization circuit of the relay 8 includes, in addition to a current supply 10 capable of feeding full wave rectified alternating current (50 Hz) to relays 7 and 8, a silicon controlled rectifier 11 the gate of which is connected to the output of a free-running multivibrator 12. In its free-running condition, the multivibrator 12 operates in cycles of about 10 seconds to maintain the silicon controlled rectifier 11 in conducting condition for about 9 seconds and in nonconducting condition for about 1 second during each cycle. As long as diathermy current flows, however, the silicon controlled rectifier 11 is maintained in conducting condition irrespective of the multivibrator 12. To this end, a sensing circuit including a coil 13 wound around the leads 5 and 6 and rectifying and smoothing elements 14 is provided to sense the presence of diathermy current in the leads 5 and 6 and apply a firing signal to the gate of the silicon controlled rectifier 11.

The energization circuit of the relay 7 includes two silicon controlled rectifiers 15 and 16 connected in series. The gate of the silicon controlled rectifier 15 is connected to the programmable unijunction transistor 9 and the gate of the silicon controlled rectifier 16 is connected to the adjustable tap 17 of a potentiometer 18. In addition to the previously mentioned switch, the relay 7 includes a second switch 7B which in the deenergized condition of the relay closes on a back contact 7BB to apply a signal to the multivibrator 12 maintaining the latter in the condition corresponding to the nonconducting condition of the silicon controlled rectifier 11.

The sensing of the impedance between the electrode segments 3A and 3B is effected by means of a 15 kHz oscillator 19 and the potentiometer 18. To this end, the oscillator 19 is connected to the electrode segment 3A, and one terminal of the potentiometer is connected to the other electrode segment 3B. The sensing circuit is completed by connecting the other terminal of the potentiometer to the oscillator.

Assuming that the segments 3A, 3B of the inactive electrode 3 are applied to the patient's skin and that the diathermy apparatus is ready for operation although no diathermy current flows, the operation of the test and control device 4 is as follows.

The oscillator 19 passes a low-voltage 15 kHz current 12 through the electrode segment 3A, the patient's skin, the electrode segment 3B and the potentiometer 18. During the first nine seconds of each sensing cycle, the free-running multivibrator 12 maintains the silicon controlled rectifier 11 in conducting condition, and consequently the relay 8 is energized to close its switch 8A on the front contact 8AF. The programmable unijunction transistor 9, which may be regarded as a complementary silicon controlled rectifier and is conducting as long as the voltage between its anode and its gate is above a predetermined value, passes a firing signal to the silicon controlled rectifier 15 to maintain the latter in conducting condition. Assuming that the impedance between the electrode segments is sufficiently low, the voltage at the potentiometer tap 17 is sufficient to maintain the silicon controlled rectifier 16 too in conducting condition so that the relay 7 is energized to close its switch 7A and to close its switch 7B on a front contact 7BF.

During the sensing interval, that is, the tenth second of the sensing cycle, the multivibrator 12 removes the firing signal from the silicon controlled rectifier 11 which is thus switched to nonconducting condition, resulting in deenergization of the relay 8 and consequent closing of the relay switch 8A on the back contact 8AB. The voltage drop over the electrode segments is thus applied between the anode and the gate of the programmable unijunction transistor 9, and if this voltage drop is above a predetermined value corresponding to a predetermined minimum value of the impedance, the programmable unijunction transistor 9 maintains its conducting condition.

If, on the other hand, the impedance between the electrode segments should be higher than the value corresponding to the setting of the adjustable potentiometer tap 17, thereby causing the voltage drop over the electrode segments to fall above the maximum permissible value, the voltage tapped at the potentiometer 18 is insufficient to maintain the silicon controlled rectifier 16 in conducting condition. The relay 7 accordingly will be deenergized to open its switch 7A, thus inhibiting the operation of the diathermy apparatus, and to close its switch 7B on the back contact 7BB. The oscillator 19 then applies a sustained signal through te lead 5 and the switch 7B to the multivibrator 12 to maintain the latter in the condition corresponding to nonconducting silicon controlled rectifier 11 and deenergized relay 8.

The operation of the diathermy apparatus will likewise be inhibited if the impedance between the electrode segments 3A and 3B falls below the minimum permissible value, e.g. because of an accidental short-circuiting of the electrode segments. In that case, the voltage between the gate and the anode of the programmable unijunction transistor 9 will be insufficient to maintain the conducting condition so that the firing signal on the gate of the silicon controlled rectifier 15 will be removed and the relay 7 accordingly will be deenergized. Normally there is no need for adjustability of the lowest permissible impedance value but as will readily be appreciated by those skilled in the art, such adjustability can easily be provided for.

An improtant feature of the invention is the use of alternating current for sensing the contact impedance of the inactive electrode segments. Since the diathermy current is an alternating current, the use of alternating current in the test and control device means that the contact impedance that is sensed is much more representative of the impedance actually encountered by the diathermy current than would be the case if direct current were used. The frequency of the sensing current is not critical but should be sufficiently high to avoid activation of the patient's muscles.

While there has been shown and described a preferred embodiment, it is to be understood that various changes, substitutions or deletions may be made by those skilled in the art without departing from the spirit and scope of the invention.

What is claimed is:

1. A test and control device for an electrosurgical diathermy current circuit of the type having a high-frequency diathermy current generator, an active electrode connected to the diathermy current generator and an inactive electrode comprising two spaced electrode segments connected in parallel to the diathermy current generator, said test and control device comprising:

a. a sensing circuit means for being connected in series through the spaced electrode segments as bridged by a patient's body including a source of alternating test current and an impedance, said sensing means comprising;

1. a free-running multivibrator having two operating states, and 2. a relay having a coil connected to and controlled by said multivibrator and a two-position switch arranged to disconnect the spaced electrode segments from the diathermy current circuit in one position;

b. means for automatically and repetitively sensing the resulting voltage drop across the electrode segments;

c. means connected to said sensing means and adapted to be connected to the diathermy current circuit and responsive to such voltage drop for inhibiting the passage of diathermy current whenever said voltage drop exceeds a predetermined maximum, or is less than a predetermined minimum said inhibiting means adapted to be connected to said electrode segments through the second position of the two-position switch; and d. circuit means controlled by said inhibiting means for applying said alternating test current to said multivibrator to hold it in that state by which said relay coil is deenergized.

2. A test and control device for an electrosurgical diathermy current circuit of the type having a high-frequency diathermy current generator, an active electrode connected to the diathermy current generator and an inactive electrode comprising two spaced electrode segments connected in parallel to the diathermy current generator, said test and control device comprising:

a. a sensing circuit means for being connected in series through the spaced electrode segments as bridged by a patient's body including a source of alternating test current and an impedance;

b. means for automatically and repetitively sensing the resulting voltage drop across the electrode segments; and c. means connected to said sensing means and adapted to be connected to the diathermy current circuit and responsive to such voltage drop for inhibiting the passsage of diathermy current whenever said voltage drop exceeds a predetermined maximum, or is less than a predetermined minimum, said inhibiting means including:

1. a relay having switch contacts adapted to be connected in the diathermy current circuit, and a coil, and 2. a pair of normally conducting electron switches each having a gate, and connected in series with said coil, one of said gates being connected to said impedance for opening its switch when said voltage drop exceeds said maximum, and the other of said gates being adapted to be connected to said electrode segments for opening its switch when said voltage drop is less than said minimum.

3. A test and control device for an electrosurgical diathermy current circuit of the type having a high-frequency diathermy current generator, an active electrode connected to the diathermy current generator and an inactive electrode comprising two spaced electrode segments connected in parallel to the diathermy current generator, said test and control device comprising:

a. a sensing circuit means for being connected in series through the spaced electrode segments as bridged by a patient's body including a source of alternating test current and an impedance;

b. means for automatically and repetitively sensing the resulting voltage drop across the electrode segments; and c. means connected to said sensing means and adapted to be connected to the diathermy current circuit and responsive to such voltage drop for inhibiting the passage of diathermy current whenever said voltage drop exceeds a predetermined maximum, or is less than a predetermined minimum, said inhibiting means including:

1. electrically controlled means having a switch adapted to be connected in the diathermy current circuit, and 2. a pair of circuit means powered by said alternating test current and normally jointly effecting energizing of said electrically controlled means, a first of said circuit means being responsive to a too low voltage on said impedance and the other of said circuit means being responsive to a too low voltage across said electrode segments.

4. A test and control device according to claim 3 in which said first of said circuit means includes a normally conducting silicon controlled rectifier controlling said electrically controlled means and having a gate connected to said impedance whereby said rectifier is rendered non-conductive in response to an excessive voltage drop across said electrode segments.

5. A test and control device according to claim 3 in which said other of said circuit means includes a normally conducting silicon controlled rectifier controlling said electrically controlled means and having a gate, an electronic switch interconnecting said source of test current with said gate and having a gate of its own adapted to be connected to the lower voltage side of said electrode segments, whereby said rectifier is rendered non-conductive in response to the absence of a voltage drop across said segments sufficient to activate said electronic switch.

* * * * *